(12) United States Patent
Frassetto

(10) Patent No.: US 8,921,572 B2
(45) Date of Patent: Dec. 30, 2014

(54) METHOD FOR PRODUCING 5,5-DISUBSTITUTED 4,5-DIHYDROISOXAZOL-3-THIOCARBOXAMIDINE SALTS

(75) Inventor: Timo Frassetto, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/511,093

(22) PCT Filed: Nov. 26, 2009

(86) PCT No.: PCT/EP2009/065925
§ 371 (c)(1),
(2), (4) Date: May 21, 2012

(87) PCT Pub. No.: WO2011/063842
PCT Pub. Date: Jun. 3, 2011

(65) Prior Publication Data
US 2012/0264947 A1    Oct. 18, 2012

(51) Int. Cl.
*C07D 261/04*    (2006.01)

(52) U.S. Cl.
CPC .................................... *C07D 261/04* (2013.01)
USPC ....................................................... 548/243

(58) Field of Classification Search
None
See application file for complete search history.

(56) References Cited

U.S. PATENT DOCUMENTS

| 6,841,519 | B1 | 1/2005 | Tamaru et al. |
| 7,238,689 | B2 | 7/2007 | Nakatani et al. |
| 7,714,142 | B2 | 5/2010 | Uchida |

FOREIGN PATENT DOCUMENTS

| EP | 1 767 528 | 3/2007 |
| EP | 1 829 868 | 9/2007 |
| JP | 2008001597 | 1/2008 |
| WO | WO 00/50410 | 8/2000 |
| WO | WO 01/12613 | 2/2001 |
| WO | WO 02/062770 | 8/2002 |
| WO | WO 2006/038657 | 4/2006 |
| WO | WO 2006/068092 | 6/2006 |
| WO | WO 2007/096576 | 8/2007 |

OTHER PUBLICATIONS

Birckenbach, Lothar, et al. "Uber Pseudohalogene. XV. Zur Reaktion der Knallsaure und ihrer Salse mit Halogenen", Justus Liebigs Annalen der Chemie 1931, p. 7-30, vol. 489, issue 1.

Mzengeza, S et al., "Asymmetric Induction in Nitrone Cycloadditions:A Total Synthesis of Acivicin by double Asymmetric Induction", Journal of Organic Chemistry, American Chemical Society, 1988, p. 4075-4081, vol. 53, No. 7, Search Report.

Mzengeza, S., et al. "A Total Synthesis of Acivicin", Journal of the American Chemical Society, 1987, p. 276-277, vol. 109, No. 1, Search Report.

Gruenanger, P. et al., "Isoxazoles", The Chemistry of Heterocyclic Compounds, John Wiley & Sons, 1991, p. 460-540, vol. 49.

Prandtl, Wilhelm, et al., "Ueber dad Trichlor-nitroso-methan das Werner Dollfus Berichte der dichlor-formoxim (phosgene-oxim) und einige ihrer derivate, 2. Mitteil: Ueber, zwei neue derivate der kohlensaeure", 1932, p. 754-759, vol. 65B, Issue 5.

English language translation of the International Preliminary Report on Patentability dated Jun. 5, 2012, from corresponding International Application No. PCT/2009/065925, filed Nov. 26, 2009.

International Search Report completed Aug. 4, 2010, in International Application No. PCT/2009/065925, filed Nov. 26, 2009.

*Primary Examiner* — Alicia L Otton
(74) *Attorney, Agent, or Firm* — Brinks Gilson & Lione

(57) ABSTRACT

A process for preparing 5,5-disubstituted 4,5-dihydroisoxazole-3-thiocarboxamidine salts of the formula (I), wherein

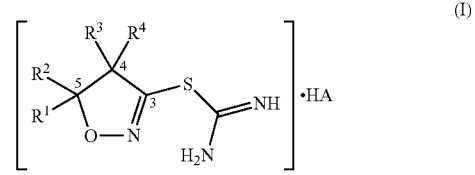

3-unsubstituted 4,5-dihydroisoxazoles are first reacted with a chlorinating or brominating reagent to give 3-halogenated 4,5-dihydroisoxazoles and the latter then react with thiourea to give the compounds of the formula (I).

11 Claims, No Drawings

METHOD FOR PRODUCING 5,5-DISUBSTITUTED 4,5-DIHYDROISOXAZOL-3-THIOCARBOXAMIDINE SALTS

This application is a National Stage application of International Application No. PCT/EP2009/065925, filed Nov. 26, 2009, the entire contents of which is hereby incorporated herein by reference.

The present invention relates to a process for preparing 5,5-disubstituted 4,5-dihydroisoxazole-3-thiocarboxamidine salts of the formula (I)

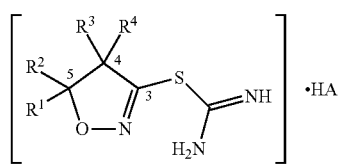

where $R^1$, $R^2$, $R^3$, $R^4$ and A are each defined as follows:

$R^1$, $R^2$ are each independently $C_1$-$C_6$-alkyl or $C_1$-$C_4$-haloalkyl;

$R^3$, $R^4$ are each independently hydrogen, halogen, $C_1$-$C_6$-alkyl or $C_1$-$C_4$-haloalkyl; or $R^1$ and $R^2$, $R^3$ and $R^4$ or $R^1$ and $R^3$ together form a $C_2$-$C_5$-alkanediyl chain which may be mono- to tetrasubstituted by $C_1$-$C_4$-alkyl and/or interrupted by oxygen or by optionally $C_1$-$C_4$-alkyl-substituted nitrogen; and A is chlorine or bromine.

5,5-Disubstituted 4,5-dihydroisoxazole-3-thiocarboxamidine salts of the formula (I) are important intermediates for the preparation of active agrochemical and pharmaceutical ingredients (WO2002/062770).

5,5-Disubstituted 4,5-dihydroisoxazole-3-thiocarboxamidine salts and processes for preparation thereof are known from the prior art. EP 1 829 868 (1) describes the reaction of 3-halogenated 4,5-dihydroisoxazoles with thiourea in the presence of acids. 3-Halogenated 4,5-dihydroisoxazoles can be prepared by 1,3-dipolar cycloaddition of nitrile oxides onto alkenes (WO2006/038657 (2), WO2000/050410 (3)). Nitrile oxides are preferably prepared in situ from dihaloformoximes and processed further directly (JP2008/001597 (4)). One alternative is the halogenation of 3-isoxazolidinones with $POCl_3$ (WO2007/096576 (5)).

An overview is given by scheme 1 below, in which R and X represent the substituents mentioned in each of the prior art documents (1), (2), (3), (4) and (5):

Scheme 1:

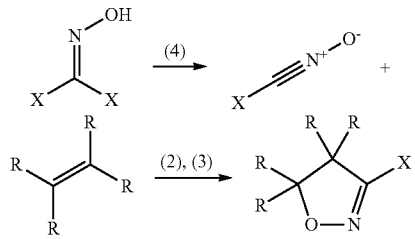

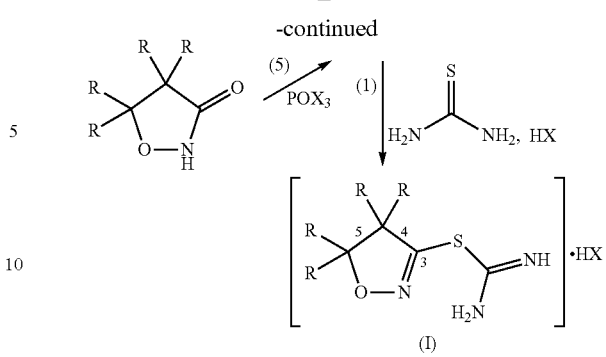

In the course of the total synthesis of acivicin, the 3 position of the 4,5-dihydroisoxazolyl moiety of an amino acid ester was chlorinated directly (J. Org. Chem., 53 (17), 4074-4081).

A disadvantage of the process according to scheme 1 is the use of unstable dihaloformoximes. In the case of the dichloro derivative, even after distillative purification, distinct decomposition is exhibited within a few days (Ber. 65B, 754-759); for the dibromo derivative, the decomposition proceeds more slowly at room temperature, but violently at elevated temperature (J. Liebigs Ann. 489, 7-30). As a consequence, the yields of the process are frequently only moderate. In addition, both compounds decompose to form toxic gases and are severe skin irritants. Furthermore, the intermediates have to be distilled with precautionary measures due to the high energy content of the compounds. In the case of use of 3-isoxazolidinones, the preparation of the starting material is found to be difficult.

The industrial scale synthesis of the compounds of the formula (I) proceeding from dihaloformoximes is also complicated by the fact that the formation of the 3-halogen-substituted 4,5-dihydroisoxazole proceeds preferentially in ethereal solvents or ethyl acetate, but the subsequent thiocarboxamidine salt formation preferentially in alcohols, nitriles or ketones. Under some circumstances, this requires a solvent exchange or performance in separate reaction vessels.

It was accordingly an object of the present invention to provide an inexpensive, economically viable and safe process, suitable for industrial scale use, for preparing 5,5-disubstituted 4,5-dihydroisoxazole-3-thiocarboxamidine salts of the formula (I).

It has been found that, surprisingly, this object is achieved by a process in which 3-unsubstituted, 5,5-disubstituted 4,5-dihydroisoxazoles of the formula (II) are first reacted with halogenating reagents in an at least equimolar amount and the resulting 3-halogenated, 5,5-disubstituted 4,5-dihydroisoxazoles of the formula (III) are reacted with at least the stoichiometric amount of thiourea to give 5,5-disubstituted 4,5-dihydroisoxazole-3-thiocarboxamidine salts of the formula (I).

The present application therefore provides a process for preparing 5,5-disubstituted 4,5-dihydroisoxazole-3-thiocarboxamidine salts of the formula (I)

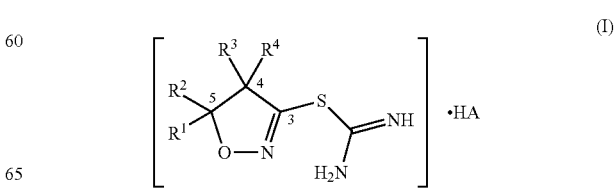

where $R^1$, $R^2$, $R^3$, $R^4$ and A are each defined as follows:

$R^1$, $R^2$ are each independently $C_1$-$C_6$-alkyl or $C_1$-$C_4$-haloalkyl;

$R^3$, $R^4$ are each independently hydrogen, halogen, $C_1$-$C_6$-alkyl or $C_1$-$C_4$-haloalkyl; or $R^1$ and $R^2$, $R^3$ and $R^4$ or $R^1$ and $R^3$ together form a $C_2$-$C_5$-alkanediyl chain which may be mono- to tetrasubstituted by $C_1$-$C_4$-alkyl and/or interrupted by oxygen or by optionally $C_1$-$C_4$-alkyl-substituted nitrogen; and A is chlorine or bromine;

wherein i) 3-unsubstituted 4,5-dihydroisoxazoles of the formula (II) are first reacted with a chlorinating or brominating reagent to give 3-halogenated 4,5-dihydroisoxazoles of the formula (III) and

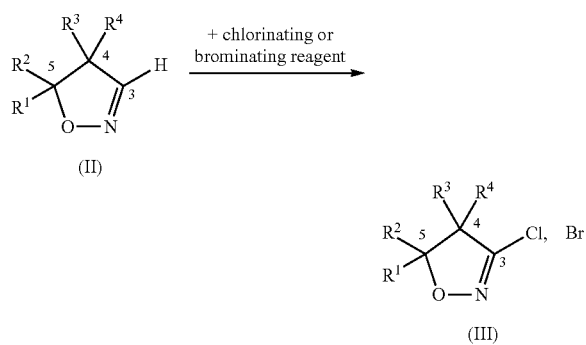

ii) the 3-halogenated 4,5-dihydroisoxazoles of the formula (III) then react with thiourea to give the compounds of the formula (I).

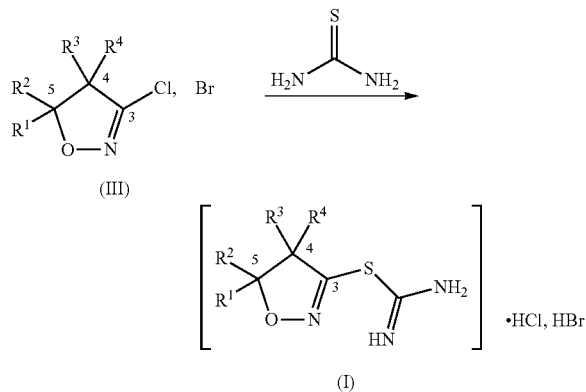

Further embodiments of the present invention can be inferred from the claims, the description and the examples. It will be appreciated that the features of the inventive subject matter which have been mentioned above and those which are still to be explained below can be used not only in the combination specified in each case but also in other combinations, without leaving the scope of the invention.

The organic molecular moieties specified for the substituents constitute collective terms for individual lists of the individual group members. Hydrocarbon chains may be straight or branched. Unless stated otherwise, halogenated substituents bear preferably from one to five identical or different halogen atoms.

The definition "halogen" in each case represents fluorine, chlorine, bromine or iodine, preferably fluorine or chlorine.

Examples of further definitions include:

Alkyl and the alkyl moieties of carboxyalkyl, sulfonylalkyl, phenylalkyl, arylalkyl, heterocyclylalkyl, heteroarylalkyl, alkoxy, alkylcarbonyl, hydroxyiminoalkyl, alkylamino, alkylcarbonyloxy, alkylsilyl and alkylsilyloxy are each a saturated, straight-chain or branched hydrocarbon group having 1 to 6 or 1 to 4 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and isomers thereof. $C_1$-$C_4$-alkyl comprises, for example, methyl, ethyl, propyl, 1-methylethyl, butyl, 1-methylpropyl, 2-methylpropyl or 1,1-dimethylethyl.

Cycloalkyl denotes monocyclic saturated hydrocarbon groups having three or more carbon atoms, for example 3 to 6 carbon ring members, such as cyclopropyl, cyclobutyl, cyclopentyl and cyclohexyl.

Haloalkyl and the haloalkyl moieties of haloalkoxy each represent partly or fully halogenated alkyl, where the halogen atom(s) is/are especially fluorine, chlorine and/or bromine, for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2-chloro-2-fluoroethyl, 2,2,2-trifluoroethyl, 2-chloro-1,1,2-trifluoroethyl, 2-chloro-2,2-difluoroethyl, 2-bromo-2,2-difluoroethyl, 2,2-dichloro-2-fluoroethyl, 2,2,2-trichloroethyl, 1,1,2,2-tetrafluoroethyl, 1,1,2,2-tetrachloroethyl, pentafluoroethyl, 2,2,3,3-tetrafluoro-1-propyl, 1,1,2,3,3,3-hexafluoro-1-propyl, 1,1,1,3,3,3-hexafluoro-2-propyl, heptafluoro-1-propyl, heptafluoro-2-propyl, 2,2,3,3,4,4,4-heptafluoro-1-butyl or nonafluoro-1-butyl.

Alkenyl and the alkenyl moieties of phenylalkenyl and alkenyloxy are each a monounsaturated, straight-chain or branched hydrocarbon group having two to six or two to four carbon atoms and a double bond in any position, for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl.

Alkynyl and the alkynyl moieties of alkynyloxy each denote straight-chain or branched hydrocarbon groups having two or more carbon atoms, for example 2 to 4, 2 to 6, or 3 to 6 carbon atoms, and one or two triple bonds in any position, but not adjacent positions, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl.

Aryl denotes a mono- to tricyclic aromatic carbocycle having 6 to 14 ring members, for example phenyl, naphthyl and anthracenyl.

Heteroaryl denotes a 5- or 6-membered aromatic ring system having one to four nitrogen atoms or having one to three nitrogen atoms and one oxygen or sulfur atom, or having one oxygen or sulfur atom.

Heterocyclyl denotes a saturated, partially unsaturated or aromatic heterocyclic ring having three or more carbon atoms, for example 3-, 4-, 5- or 6-membered heterocyclic ring which comprises one to four identical or different heteroatoms selected from the group of oxygen, sulfur and nitrogen, and may be bonded via C or N; where one sulfur in heterocyclyl may be oxidized to S=O or S(=O)$_2$, and where a bicyclic ring system may be formed with a fused-on phenyl ring or with a C$_3$-C$_6$-carbocycle or with a further 5- to 6-membered heterocycle.

In the process according to the invention, preference is given to using compounds of the formula (II) whose variables are defined as follows, specifically in each case alone or in combination:
$R^1$ is C$_1$-C$_6$-alkyl or C$_1$-C$_4$-haloalkyl;
$R^2$ is C$_1$-C$_6$-alkyl or C$_1$-C$_4$-haloalkyl;
$R^3$ is hydrogen, halogen, C$_1$-C$_6$-alkyl, C$_1$-C$_4$-haloalkyl and
$R^4$ is hydrogen, halogen, C$_1$-C$_6$-alkyl, C$_1$-C$_4$-haloalkyl; or $R^1$ and $R^2$, $R^3$ and $R^4$ or $R^1$ and $R^3$ form a C$_2$-C$_5$-alkanediyl chain.

Particular preference is given to using compounds of the formula (II) whose variables are defined as follows, specifically in each case alone or in combination:
$R^1$ is C$_1$-C$_4$-alkyl, especially methyl or ethyl, more preferably methyl;
$R^2$ is C$_1$-C$_4$-alkyl, especially methyl or ethyl, more preferably methyl;
$R^3$ is hydrogen, fluorine, chlorine, bromine, methyl, ethyl, more preferably hydrogen; and
$R^4$ is hydrogen, fluorine, chlorine, bromine, methyl, ethyl, more preferably hydrogen.

Exceptional preference is given to using the compound of the formula (IIa) whose variables are defined as follows:
$R^1$ is methyl;
$R^2$ is methyl;
$R^3$ is hydrogen;
$R^4$ is hydrogen.

In the process according to the invention, the compound of the formula (IIa) is converted to the compound of the formula (Ia):

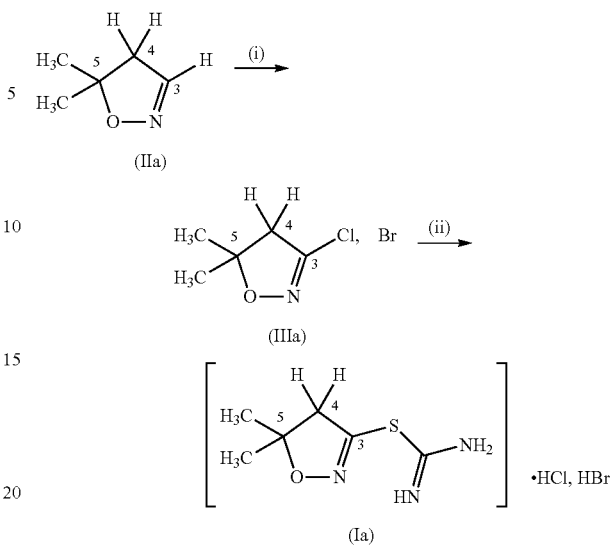

Particular 5,5-disubstituted 4,5-dihydroisoxazole-3-thiocarboxamidine salts of the formula (I) where $R^3$, $R^4$ are each independently defined as hydrogen, fluorine or chlorine are, for example, intermediates in a process for preparing oxazole herbicides of the formula (IV)

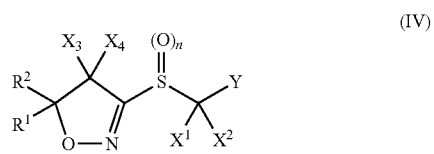

where the variables are each defined as follows:

n is 0, 1 or 2;

$X^1$, $X^2$, $X^3$, $X^4$ are each independently hydrogen, fluorine or chlorine; and Y is phenyl, 6-membered heteroaryl having one to three nitrogen atoms or 5-membered heteroaryl having one to three heteroatoms selected from the group of oxygen, nitrogen and sulfur, where phenyl and heteroaryl may each be substituted by one to five substituents selected from the group of halogen, nitro, cyano, C$_1$-C$_4$-alkyl, C$_3$-C$_6$-cycloalkyl, C$_1$-C$_4$-haloalkyl, carboxy-C$_1$-C$_4$-alkyl, sulfonyl-C$_1$-C$_4$-alkyl, C$_2$-C$_6$-alkenyl, C$_2$-C$_6$-alkynyl, C$_1$-C$_4$-alkoxy, C$_1$-C$_4$-haloalkoxy, C$_2$-C$_6$-alkenyloxy, C$_2$-C$_6$-alkynyloxy and C$_1$-C$_4$-alkylcarbonyloxy; and $R^1$, $R^2$ are each independently C$_1$-C$_6$-alkyl or C$_1$-C$_4$-haloalkyl; or $R^1$ and $R^2$ together form a C$_2$-C$_5$-alkanediyl chain which may be mono- to tetrasubstituted by C$_1$-C$_4$-alkyl and/or may be interrupted by oxygen or by optionally C$_1$-C$_4$-alkyl-substituted nitrogen.

Oxazole herbicides of the formula (IV) are known from WO 02/062770 and WO 01/012613.

The 5,5-disubstituted 4,5-dihydroisoxazole-3-thiocarboxamidine salt of the formula (Ia) where $R^1$ and $R^2$ are each defined as methyl and $R^3$ and $R^4$ are each defined as hydrogen is preferably used as an intermediate in processes for preparing oxazole herbicides of the formula (IVB) where

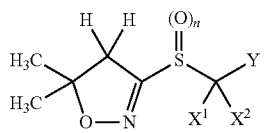
(IVB)

n is 1 or 2;

$X^1$, $X^2$ are each independently hydrogen or fluorine; and

Y is phenyl, where phenyl may be substituted by one to three substituents selected from the group of halogen, $C_1$-$C_4$-alkyl, $C_1$-$C_4$-haloalkyl and $C_1$-$C_4$-alkoxy.

More particularly, the 5,5-disubstituted 4,5-dihydroisoxazole-3-thiocarboxamidine salt of the formula (Ia) where $R^1$ and $R^2$ are each defined as methyl and $R^3$ and $R^4$ are each defined as hydrogen is used as an intermediate in processes for preparing oxazole herbicides of the formula (IVA) too where

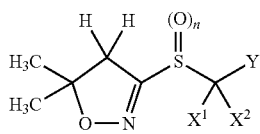
(IVA)

n is 1 or 2;

$X^1$, $X^2$ are each independently hydrogen or fluorine; and

Y is pyrazolyl which may be substituted by one to three substituents selected from the group of $C_1$-$C_4$-alkyl, $C_1$-$C_4$-haloalkyl and $C_1$-$C_4$-haloalkoxy.

Exceptionally preferably, the 5,5-disubstituted 4,5-dihydroisoxazole-3-thiocarboxamidine salt of the formula (Ia) where $R^1$ and $R^2$ are each defined as methyl and $R^3$ and $R^4$ are each defined as hydrogen is used as an intermediate in processes for preparing oxazole herbicides of the formulae (IVa) and (IVb).

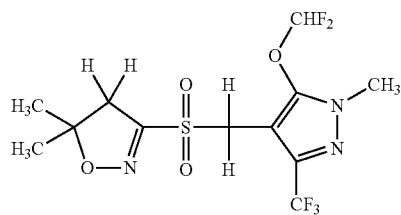
(IVa)

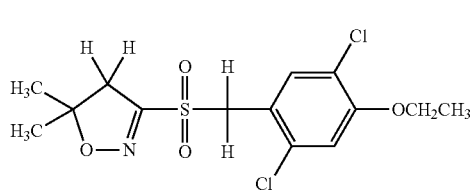
(IVb)

Proceeding from the intermediate of the formula (Ia), the further steps in the process for preparing the oxazole herbicide of the formula (IVa), for example, are already known per se to those skilled in the art or have been described in the literature.

The preparation of the pyrazole (c) from dicarbonyl compounds and hydrazines is demonstrated, for example, in JP2007/031342. The reaction of the hydroxyl-substituted pyrazole with formaldehyde, followed by the reaction with thiocarboxamidine salts (d) is described in CA 2 560 936 (WO2005/095352). The alkylation of the hydroxyl group (e) is known to those skilled in the art from JP2007/246396. The final oxidation of the sulfur to the sulfone (f) is employed, for example, in EP 1 405 853.

For the compound of the formula (IVa), one possible synthesis can be illustrated as follows:

Scheme 2a:

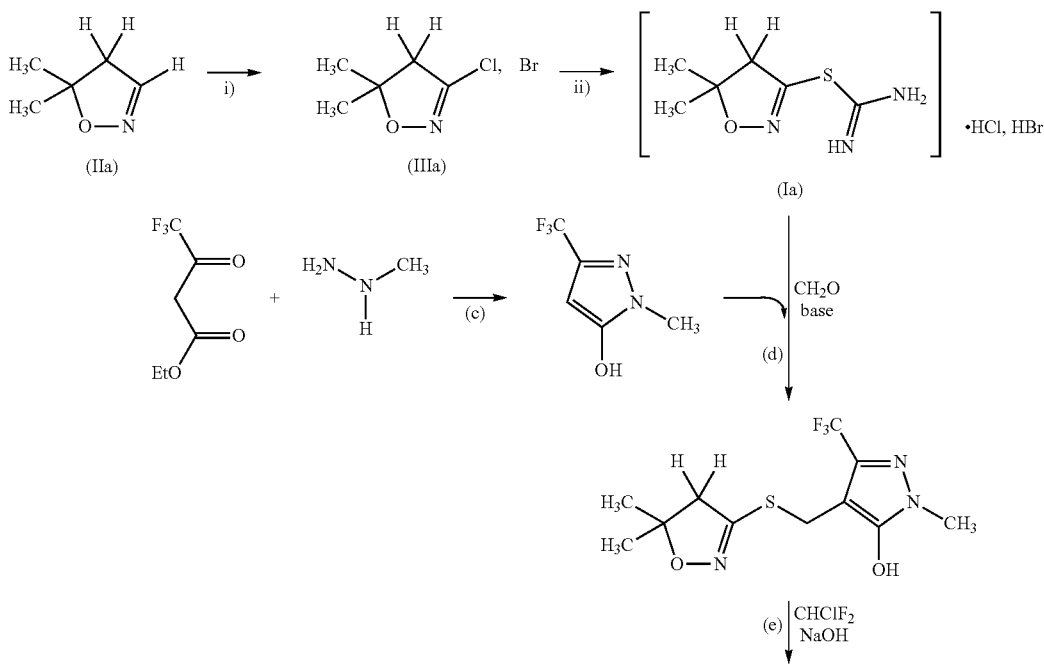

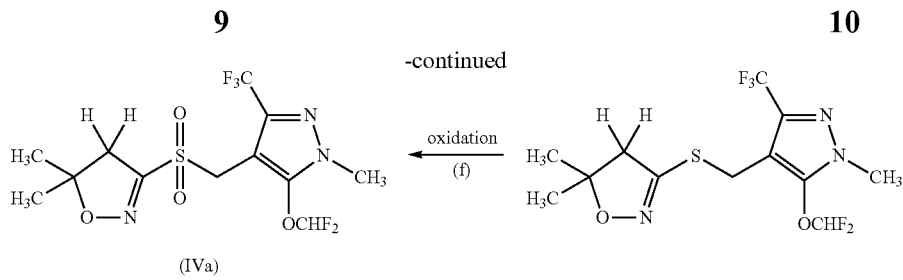

(IVa)

Proceeding from the intermediate of the formula (Ia), the further steps in the process for preparing the oxazole herbicide of the formula (IVb), for example, are already known per se to those skilled in the art or have been described in the literature.

The nucleophilic substitution of benzylic bromides (g) has been demonstrated, for example, in WO2007/096576. The final oxidation of the sulfur to the sulfone (h) is employed, for example, in EP 1 405 853.

For the compound of the formula (IVb), one possible synthesis can be illustrated as follows:

Scheme 2b:

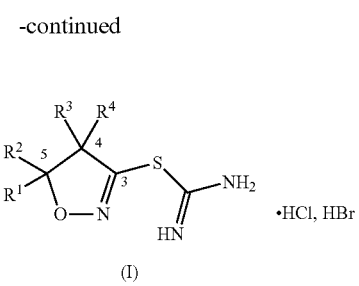

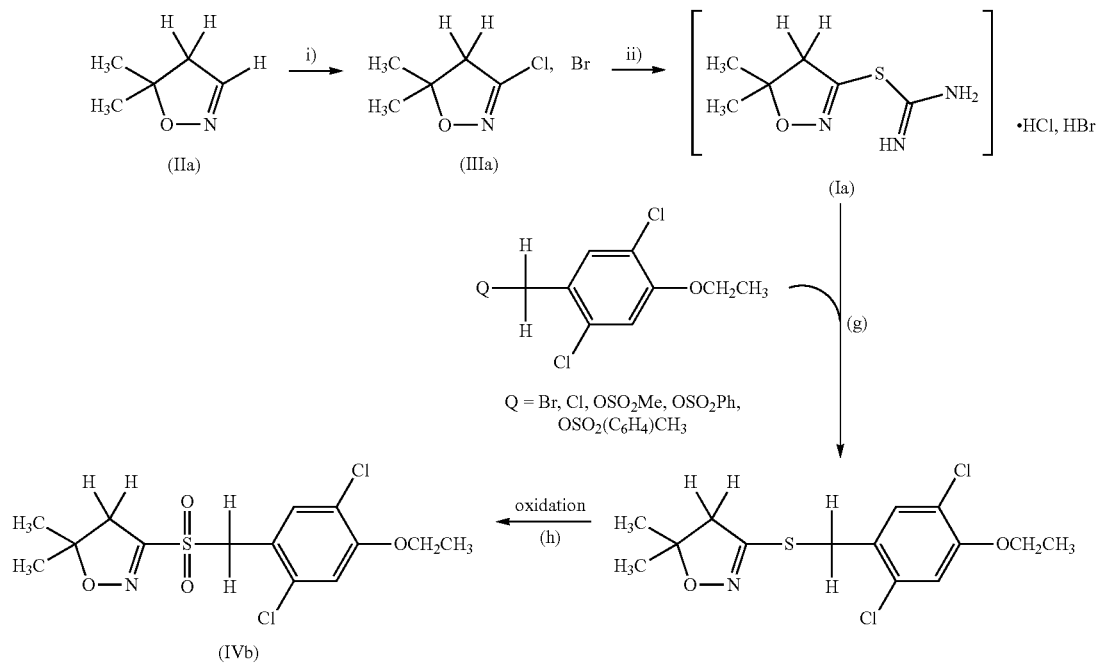

The process of the invention can be illustrated schematically as follows:

Scheme 3:

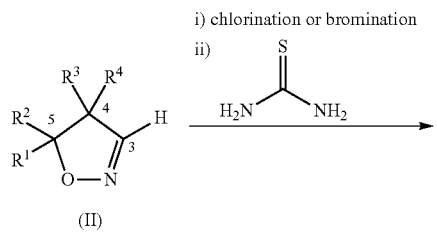

3-Unsubstituted 4,5-dihydroisoxazoles of the formula (II) are commercially available or can alternatively be prepared according to Grünanger, P.; Vita-Finzi, P.: Isoxazoles in Taylor, E. C.: *The Chemistry of Heterocyclic Compounds Vol. 49*, Wiley & Sons. Inc., New York, 1991, p. 460-540.

The process according to the invention is generally performed under the following conditions:

The compound of the formula (II) can be used as a pure substance or as a crude product from the formation reaction. For this purpose, the 3-unsubstituted 4,5-dihydroisoxazole of the formula (II) can either be dissolved or suspended in a suitable solvent, or it is present dissolved or suspended in a suitable solvent from the formation reaction.

Suitable solvents or diluents for steps i) and ii) are those which are inert under the reaction conditions, for example alcohols, chlorinated aromatic or chlorinated aliphatic hydrocarbons, esters, ethers, amides, nitriles or mixtures of these solvents. Preference is given to using alcohols, especially tertiary alcohols such as tert-butanol or tert-amyl alcohol, chlorinated aromatic or chlorinated aliphatic hydrocarbons such as chlorobenzene and chloroform as solvents. Exceptionally preferably, tert-butanol is used.

Surprisingly, tert-butanol is found to be advantageous compared to primary aliphatic alcohols, since it exhibits only a negligible tendency to form 3-alkoxy-4,5-dihydroisoxazoles, which have been found to be unreactive in the subsequent reaction with thiourea (comparative example 1).

For reaction steps i) and ii) of the process according to the invention, it is possible to use different solvents and diluents among those mentioned above in each case. In a preferred embodiment, reaction steps i) and ii) are performed in the same solvent or diluent; in a particularly preferred embodiment, both steps, i) and ii), are performed in tert-butanol.

The amount of solvent or diluent is generally selected such that the reaction mixtures remain free-flowing during the reaction. In a preferred embodiment, less than 1 l and preferably less than 500 ml of solvent is used per mole of the 3-unsubstituted 4,5-dihydroisoxazole of the formula (II). These figures are based on the total amount of solvent in reaction stages i) and ii). It will be appreciated that, for reasons of cost, minimum amounts of solvents will be used. In general, therefore, the amount of solvent will not be more than 5 l per mole of the 3-unsubstituted 4,5-dihydroisoxazole of the formula (II).

The compound of the formula (II) is converted to 3-halogenated 4,5-dihydroisoxazoles by reaction with halogenating reagents, the reagent being used in an equimolar amount or in an up to 10-fold excess, preferably in an equimolar amount or in an up to 1.5-fold excess.

Suitable reagents are, for example, elemental chlorine or bromine, aqueous solutions of hypochlorite, hypobromite, solutions of inorganic bromides and chlorides such as HCl, HBr, NaCl, KCl, NaBr or KBr in the presence of an oxidizing agent such as hydrogen peroxide, potassium peroxomonosulfate or organic peroxides such as tert-butyl hydroperoxide, the combination of bromine and hydrogen peroxide, organic hypochlorites such as tert-butyl hypochlorite, trichloroisocyanuric acid, thionyl chloride or sulfuryl chloride, N-bromosuccinimide, N-chlorosuccinimide or 1,3-dibromo-5,5-dimethylhydantoin.

The halogenating reagents can be used as a pure substance or as a solution in one of the solvents specified above.

Particular preference is given to the halogens bromine and chlorine.

In an exceptionally preferred embodiment, chlorine gas is introduced into the reaction solution until the starting material has been converted completely. The course of the reaction can be monitored by means of methods known to those skilled in the art, for example by HPLC analysis of the resulting reaction product.

The reaction is effected at temperatures between −30° C. and 150° C., preferably at temperatures between −10° C. and 30° C.

The reaction product from step i), 3-halogenated 4,5-dihydroisoxazole of the formula (III), can be reacted in the process according to the invention, directly without purification or after a purification, in step ii) with thiourea to give 4,5-dihydroisoxazole-3-thiocarboxamidine salts of the formula (I).

The reaction product from step i), 3-halogenated 4,5-dihydroisoxazole of the formula (III), can be purified in a customary manner, for example by distillation, crystallization, precipitation, extraction or chromatography, preferably by distillation.

In a preferred embodiment of the process according to the invention, the reaction product from step i), 3-halogenated 4,5-dihydroisoxazole of the formula (III), is reacted directly without purification in step ii) with thiourea to give 4,5-dihydroisoxazole-3-thiocarboxamidine salts of the formula (I).

In a particularly preferred embodiment of the process according to the invention, the reaction product from step i), 3-halogenated 4,5-dihydroisoxazole of the formula (III), is reacted directly without purification in step ii) with thiourea to give 4,5-dihydroisoxazole-3-thiocarboxamidine salts of the formula (I) in the same reaction vessel, i.e. in a one-pot process.

After the halogenation in step i), optionally after purification of the reaction product, purging of the reaction vessel with nitrogen or application of a vacuum, the conversion to the 5,5-disubstituted 4,5-dihydroisoxazole-3-thiocarboxamidine salts of the formula (I) is performed by addition of thiourea.

In general, thiourea is added a little at a time in solid form in step ii), until the reaction has ended. Preference is given to adding thiourea in an equimolar amount or in an up to 1.2-fold excess, based on the 3-halogenated 4,5-dihydroisoxazole present in the reaction mixture.

The reaction is effected at temperatures between 0° C. and 100° C., preferably between room temperature and 50° C.

Surprisingly, the reaction with thiourea in step ii) of the process according to the invention in tert-butanol proceeds rapidly in a smooth reaction even without additional addition of acid. In EP 1 829 868, in a comparative example, the reaction of isolated 3-chloro-5,5-dimethyl-4,5-dihydroisoxazole with thiourea in ethanol without addition of acid affords the desired thiocarboxamidine salt with only 10% yield after 10 h at 30° C. The process according to the invention for preparing 5,5-disubstituted 4,5-dihydroisoxazole-3-thiocarboxamidine salts affords the corresponding 5,5-disubstituted 4,5-dihydroisoxazole-3-thiocarboxamidine salts in very high yields. Additional addition of acid is not required in the process according to the invention.

The reaction mixture obtained in step ii) is worked up in a manner customary per se. For example, the product of the process according to the invention, 5,5-disubstituted 4,5-dihydroisoxazole-3-thiocarboxamidine salt of the formula (I), after removal of the solvent, can be purified by recrystallization. In a preferred embodiment, the product precipitates out of the reaction medium in crystalline form, optionally after concentration of the reaction solution or addition of an antisolvent, for example a nonpolar solvent such as acetone or toluene.

In one embodiment of the process according to the invention, the 3-unsubstituted 5,5-disubstituted 4,5-dihydroisoxazole of the formula (IIb) where $R^1$ and $R^2$ are each $C_1$-$C_6$-alkyl or $C_1$-$C_4$-haloalkyl; or $R^1$ and $R^2$ together form a $C_2$-$C_5$-alkanediyl chain which may be mono- to tetrasubstituted by $C_1$-$C_4$-alkyl and/or may be interrupted by oxygen or by optionally $C_1$-$C_4$-alkyl-substituted nitrogen; and $R^3$ and $R^4$ are each hydrogen; is prepared in a preliminary stage and, optionally after solvent exchange, used further directly in the process according to the invention.

The preliminary stage of the process according to the invention is a process for preparing 5,5-disubstituted 4,5-dihydroisoxazoles of the formula (IIb)

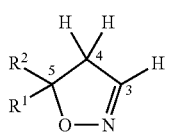

(IIb)

where

R¹, R² are each independently $C_1$-$C_6$-alkyl or $C_1$-$C_4$-haloalkyl; or R¹ and R² together form a $C_2$-$C_5$-alkanediyl chain which may be mono- to tetrasubstituted by $C_1$-$C_4$-alkyl and/or may be interrupted by oxygen or by optionally $C_1$-$C_4$-alkyl-substituted nitrogen;

wherein an oxime of the formula (AII)

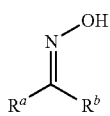

(AII)

where $R^a$, $R^b$ are each independently hydrogen, $C_1$-$C_6$-alkyl, $C_1$-$C_4$-alkylcarbonyl, hydroxyimino-$C_1$-$C_4$-alkyl, phenyl, phenyl-$C_1$-$C_4$-alkyl or phenyl-$C_2$-$C_4$-alkenyl, where the phenyl rings may be mono- or polysubstituted by $C_1$-$C_4$-alkyl, $C_1$-$C_4$-alkoxy, Di-$C_1$-$C_4$-alkylamino, halogen, hydroxyl or nitro; or $R^a$ and $R^b$ together form a $C_2$-$C_5$-alkanediyl chain;

is reacted with a carbonyl compound of the formula (AIII)

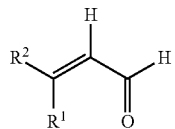

(AIII)

where R¹ and R² are each as defined above;

in the presence of a catalyst and optionally in the presence of a solvent.

For the preliminary stage of the process according to the invention, preference is given to using compounds of the formulae (AII) and (AIII) where the variables, in each case alone or in combination, are each defined as follows:

R¹ is $C_1$-$C_6$-alkyl or $C_1$-$C_4$-haloalkyl;
R² is $C_1$-$C_6$-alkyl or $C_1$-$C_4$-haloalkyl;
$R^a$ is hydrogen, $C_1$-$C_6$-alkyl, $C_1$-$C_4$-alkylcarbonyl, hydroxyimino-$C_1$-$C_4$-alkyl; and
$R^b$ is $C_1$-$C_6$-alkyl; or $R^a$ and $R^b$ form a $C_2$-$C_5$-alkanediyl chain.

Particular preference is given to using compounds of the formulae (AII) and (AIII) where the variables, in each case alone or in combination, are each defined as follows:

R¹ is $C_1$-$C_4$-alkyl, especially methyl or ethyl, more preferably methyl;
R² is $C_1$-$C_4$-alkyl, especially methyl or ethyl, more preferably methyl;
$R^a$ is hydrogen, $C_1$-$C_4$-alkyl, especially methyl, ethyl, isopropyl or isobutyl, more preferably methyl and ethyl; and
$R^b$ is $C_1$-$C_4$-alkyl, especially methyl or ethyl; or $R^a$ and $R^b$ form a $C_2$-$C_5$-alkanediyl chain.

Exceptional preference is given to using compounds of the formulae (AII) and (AIII) where the variables, in each case alone or in combination, are each defined as follows:

R¹ is methyl;
R² is methyl;
$R^a$ is methyl or ethyl;
$R^b$ is methyl or ethyl.

For the preliminary stage of the process according to the invention, the oxime of the formula (AII) is reacted with the carbonyl compound of the formula (AIII) in the presence of an acid catalyst or of an acid-base catalyst and optionally in the presence of an organic solvent (scheme 4):

Scheme 4:

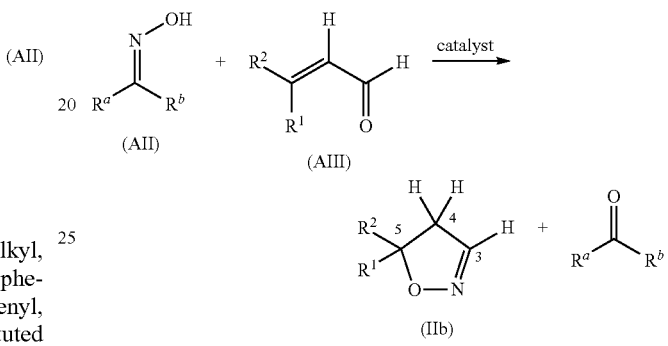

The oximes of the formula (AII) are either commercially available or can be prepared, for example, according to Yamane, M.; Narasaka, K., in *Science of Synthesis*, 27 (2004), p. 605.

The carbonyl compounds of the formula (AIII) are likewise commercially available or can be prepared, for example, according to Escher, I.; Glorius, F., in *Science of Synthesis*, 25 (2006), p. 733.

In general, the process according to the invention for preparing the compound of the formula (IIb) is performed under the following conditions:

The oxime of the formula (AII) and the carbonyl compound of the formula (AIII) are used in the process according to the invention in a molar ratio of 3:1 to 1:3. The excess of one of the two components is preferably up to 20 mol %, especially of the carbonyl compound of the formula (AIII). The preferred molar ratio of the oxime (AII) to the carbonyl compound (AIII) is correspondingly 1.0:0.8 to 1.0:1.2, more preferably about 1.0:1.0 to 1.0:1.1.

The reaction of the oxime of the formula (AII) and of the carbonyl compound of the formula (AIII) takes place in the presence of a catalyst. Suitable catalysts are particular acids (acid catalyst) or mixtures of particular acids and particular bases (acid-base catalyst).

The acid-catalyzed process according to the invention can be illustrated schematically as follows:

Scheme 5:

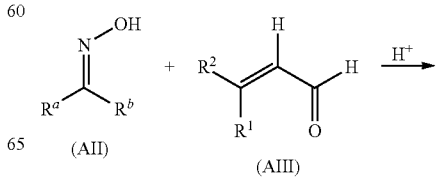

-continued

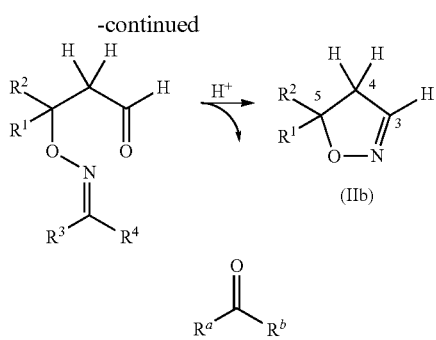

Suitable acid catalysts are proton donors (Brønsted acids), for example inorganic and organic acids. Examples of inorganic acids are hydrohalic acids and oxygen acids, especially hydrochloric acid, sulfuric acid, nitric acid, phosphoric acid, phosphonic acid and phosphinic acid.

Examples of organic acids are aliphatic and aromatic acids such as alkylsulfonic acids, arylsulfonic acids, mono-$C_1$-$C_6$-alkyl phosphates, di-$C_1$-$C_6$-alkyl phosphates, monoaryl phosphates, diaryl phosphates, alkylcarboxylic acids, haloalkylcarboxylic acids and heterocyclylcarboxylic acids, especially methanesulfonic acid, p-toluenesulfonic acid, citric acid, trifluoroacetic acid and proline.

In general, the reaction proceeds under acid catalysis in good yield with those acids whose pKa is less than 3.5.

If the process according to the invention is performed under acid catalysis, preference is given to strong acids such as phosphoric acid, mono-$C_1$-$C_6$-alkyl phosphates, di-$C_1$-$C_6$-alkyl phosphates, monoaryl phosphates, diaryl phosphates, sulfuric acid, sulfonic acids or trifluoroacetic acid.

The acid-base-catalyzed process according to the invention could proceed according to the following scheme:

Scheme 6:

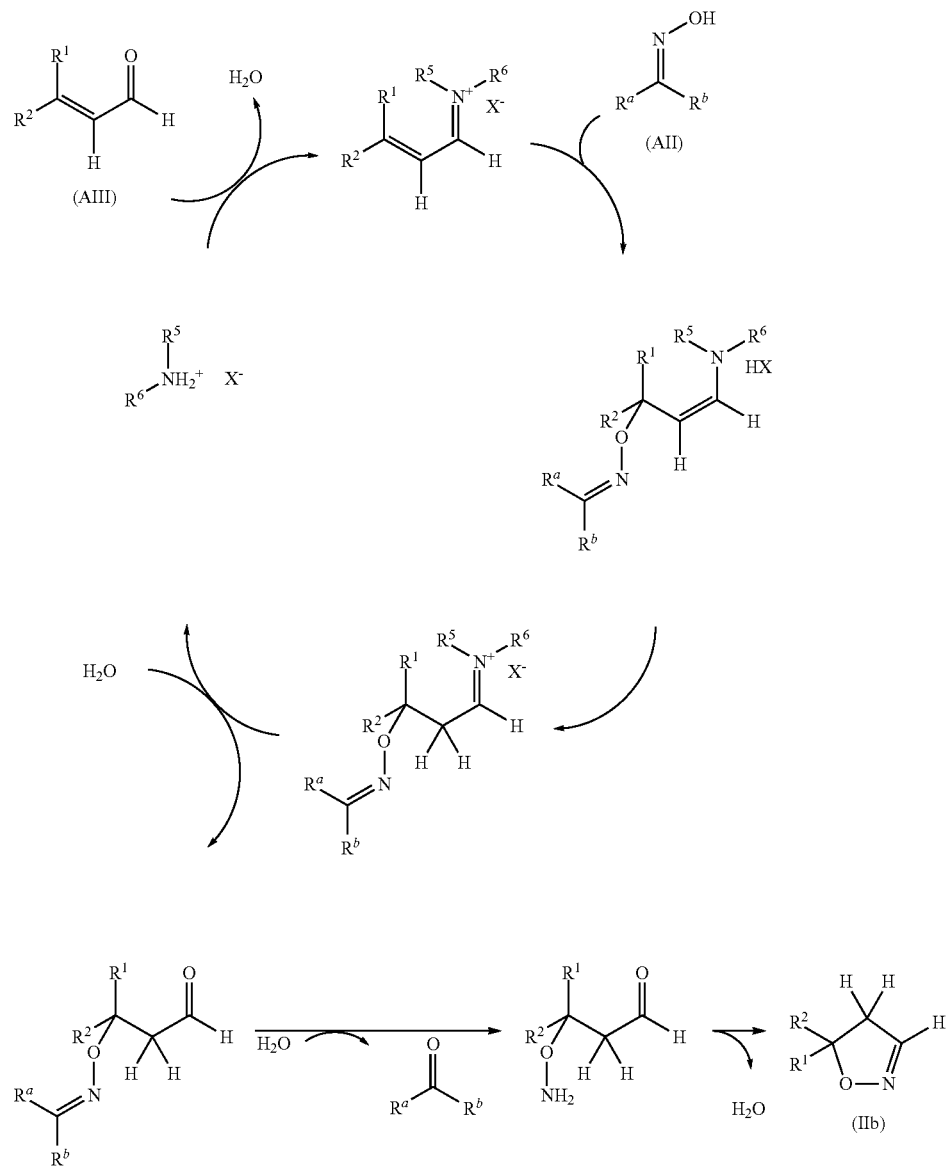

Suitable acid-base catalysts are mixtures of the above-described acids and particular bases, acid and base being usable separately from one another or as an acid addition salt.

Suitable bases have been found to be compounds which comprise one or more heteroatoms, for example nitrogen, oxygen, sulfur or phosphorus, nitrogen being a preferred heteroatom.

Examples of such bases are primary or secondary amines of the formula (V)

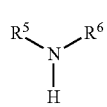

(V)

where $R^5$ and $R^6$ are each independently $C_1$-$C_6$-alkyl, $C_3$-$C_6$-cycloalkyl, $C_2$-$C_6$-alkenyl, $C_2$-$C_6$-alkynyl, tri-$C_1$-$C_6$-alkylsilyl, aryl, aryl-$C_1$-$C_6$-alkyl, heteroaryl, heteroaryl-$C_1$-$C_6$-alkyl, and where the aryl and heteroaryl moieties of the substituents may themselves be substituted by one to three substituents selected from the group of halogen, nitro, cyano, $C_1$-$C_4$-alkyl, $C_3$-$C_6$-cycloalkyl, $C_1$-$C_4$-haloalkyl, carboxy-$C_1$-$C_4$-alkyl, $C_2$-$C_6$-alkenyl, $C_2$-$C_6$-alkynyl, $C_1$-$C_4$-alkoxy, $C_1$-$C_4$-haloalkoxy, $C_2$-$C_6$-alkenyloxy, $C_2$-$C_6$-alkynyloxy, $C_1$-$C_4$-alkylcarbonyloxy;
and where $R^5$ may additionally be hydrogen.

Preference is given to compounds of the formula (V) in which $R^5$ and $R^6$ are each independently $C_1$-$C_6$-alkyl, $C_3$-$C_6$-cycloalkyl, tri-$C_1$-$C_6$-alkylsilyl, aryl or aryl-$C_1$-$C_6$-alkyl;
and where the aryl moieties of the substituents may themselves be substituted by one to three substituents selected from the group of halogen, nitro, cyano, $C_1$-$C_4$-alkyl, $C_3$-$C_6$-cycloalkyl, $C_1$-$C_4$-haloalkyl, carboxy-$C_1$-$C_4$-alkyl, $C_2$-$C_6$-alkenyl, $C_2$-$C_6$-alkynyl, $C_1$-$C_4$-alkoxy, $C_1$-$C_4$-haloalkoxy, $C_2$-$C_6$-alkenyloxy, $C_2$-$C_6$-alkynyloxy, $C_1$-$C_4$-alkylcarbonyloxy;
and where $R^5$ may additionally be hydrogen.

Particular preference is given to compounds of the formula (V) in which $R^5$ and $R^6$ are each independently methyl, ethyl, propyl, 1-methylethyl, butyl, cyclopentyl, cyclohexyl, phenyl, naphthyl, benzyl or trimethylsilyl; and where $R^5$ may additionally be hydrogen; for example N-methylaniline.

Alternatively, $R^5$ and $R^6$ together may form a ring structure of the formula (VI)

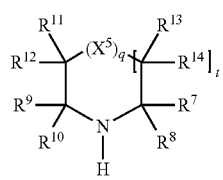

(VI)

where
$X^5$ is O, S, $NR^{15}$ or $CR^{16}R^{17}$;
q is 0 or 1;
t is 0 or 1; and
$R^7$, $R^8$, $R^9$, $R^{10}$, $R^{11}$, $R^{12}$, $R^{13}$, $R^{14}$, $R^{16}$, $R^{17}$ are each independently selected from hydrogen, hydroxyl, carboxyl, amino, nitro, aminocarbonyl, $C_1$-$C_6$-alkyl, $C_1$-$C_6$-alkoxy, $C_1$-$C_6$-alkylcarbonyl, mono-$C_1$-$C_6$-alkylamino, di-$C_1$-$C_6$-alkylamino, aryl, heteroaryl, aryl-$C_1$-$C_6$-alkoxy, and where $C_1$-$C_6$-alkyl may itself be substituted by aryl, heteroaryl, heterocyclyl or trimethylsilyloxy and where the aryl, heterocyclyl and heteroaryl moieties of the substituents may themselves be substituted by one to three substituents selected from the group of halogen, nitro, cyano, $C_1$-$C_4$-alkyl, $C_3$-$C_6$-cycloalkyl, $C_1$-$C_4$-haloalkyl, carboxy-$C_1$-$C_4$-alkyl, $C_2$-$C_6$-alkenyl, $C_2$-$C_6$-alkynyl, $C_1$-$C_4$-alkoxy, $C_1$-$C_4$-haloalkoxy, $C_2$-$C_6$-alkenyloxy, $C_2$-$C_6$-alkynyloxy and $C_1$-$C_4$-alkylcarbonyloxy;
or $R^{11}$ and $R^{12}$ and/or $R^{13}$ and $R^{14}$ form, together with the carbon atom to which they are bonded, a keto group; and $R^{15}$ is selected from hydrogen, $C_1$-$C_6$-alkyl, Aryl-$C_1$-$C_6$-alkyl.

Preference is given to amines of the formula (V) or (VI) where $R^5$ and $R^6$ together with the NH group form an imidazolin-5-one ring of the formula (VII)

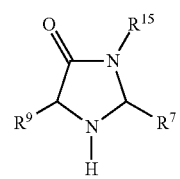

(VII)

where the substituents are each as defined above.

Particular preference is given here to compounds in which $R^7$ and $R^9$ are each independently selected from $C_1$-$C_6$-alkyl and aryl-$C_1$-$C_6$-alkyl, preferably from methyl, ethyl, 1-methylethyl, 1,1-dimethylethyl and phenylmethyl.

In general, the catalysts are added to the reaction mixture in a catalytic amount. In one embodiment of the invention, the molar ratio of the compound of the formula (AII) to the acid catalysts or to the acid-base catalysts is less than 1:0.1. In a preferred embodiment, the molar ratio is less than 1:0.05, in a particularly preferred embodiment less than 1:0.02.

The oxime of the formula (AII) and the carbonyl compound of the formula (AIII) can, in accordance with the invention, be converted either without addition of a solvent or with addition of a suitable solvent.

In one embodiment of the process according to the invention, the oxime of the formula (AII) and the carbonyl compound of the formula (AIII) are reacted with one another with addition of a solvent.

The amount of solvent or diluent is generally selected such that the reaction mixtures remain free-flowing during the reaction.

In a preferred embodiment of the process according to the invention, the proportion of the solvent in the reaction mixture, i.e. before the start of the reaction, is less than 80% by weight.

Suitable solvents are organic solvents, for example aromatic hydrocarbons such as toluene, o-, m-, p-dimethylbenzene, 1,3,5-trimethylbenzene, ethylbenzene, chlorobenzene, o-, m-, p-dichlorobenzene, halogenated aliphatic hydrocarbons such as tetrachloroethane, trichloromethane, dichloromethane and dichloroethene, aliphatic hydrocarbons such as pentane, hexane, heptane, octane, cyclopentane, methylcyclopentane and cyclohexane, ethers such as diethyl ether, methyl tert-butyl ether, tetrahydrofuran and dioxane, alcohols such as methanol, ethanol, propanol, tertiary alcohols such as tert-butanol and tert-amyl alcohol, esters such as ethyl acetate, nitriles such as acetonitrile, or mixtures of the solvents mentioned.

Preferred solvents are aromatic hydrocarbons, halogenated aliphatic hydrocarbons, aliphatic hydrocarbons, ethers and alcohols.

Particularly preferred solvents are aromatic hydrocarbons, especially toluene, chlorobenzene, o-, m-dichlorobenzene, tertiary alcohols such as tert-butanol and tert-amyl alcohol and mixtures of these solvents.

In an exceptionally preferred embodiment of the invention, the process for preparing the 3-unsubstituted 5,5-disubstituted 4,5-dihydroisoxazole of the formula (II) is performed in the same solvent as the subsequent halogenation and thiocarboxamidine salt formation to prepare the 5,5-disubstituted 4,5-dihydroisoxazole-3-thiocarbamidine salt of the formula (I) in the process according to the invention, especially in tert-butanol.

In general, the sequence in which the oxime of the formula (AII), the carbonyl compound of the formula (AIII), the catalyst and, if appropriate, the solvent are initially charged in or added to the reaction vessel is unimportant.

In one embodiment of the invention, the oxime of the formula (AII) and the carbonyl compound of the formula (AIII) and, if appropriate, the solvent are initially charged and the desired temperature is established. Then the catalyst is added.

In another embodiment of the invention, the oxime of the formula (AII), the catalyst and, if appropriate, the solvent are initially charged and the desired temperature is established. Then the carbonyl compound of the formula (AIII) is added.

Addition is understood to mean the addition of a substance, either a little at a time or continuously. The catalyst and the carbonyl compound of the formula (AIII) are added preferably without solvent or dissolved in an organic solvent as defined above in the course of the reaction.

It is normal to work at a reaction temperature of −40 to 100° C., preferably of −20 to 60° C., especially of 0 to 30° C.

The reaction mixture can be sent directly to other processes without further workup or after removal of the carbonyl compound formed. The carbonyl compound is removed by methods known to those skilled in the art, for example by distillation or filtration. The reaction product, the 5,5-disubstituted 4,5-dihydroisoxazole of the formula (II), can also be removed from the reaction mixture, for example by direct distillation, extraction or chromatography, preferably by distillation.

In a preferred embodiment of the process according to the invention, the reaction product of the preliminary stage, the 3-unsubstituted 5,5-disubstituted 4,5-dihydroisoxazole of the formula (IIb), after distillative removal of the carbonyl compound formed, can be used further directly in step i) of the process according to the invention for preparation of the compound of the formula (I).

EXAMPLES

Example 1

Acid-Base Catalysis

Synthesis of 5,5-dimethyl-4,5-dihydroisoxazole 10.0 g (0.137 mol; 100 mol %) of acetone oxime were admixed with 12.7 g (0.151 mol, 110 mol %) of 3-methyl-2-butenal and cooled to 10° C. Over the course of 3 h, a mixture of 0.13 g (1.2 mmol, 0.9 mol %) of N-methylaniline and 0.14 g (1.2 mmol, 0.9 mol %) of trifluoroacetic acid was added a little at a time to this mixture, and the temperature was increased to 22° C. after 20% of the addition. After 3 h, the product of value was isolated from the reaction mixture by fractional distillation under reduced pressure. Boiling point 44-48° C. at 17-18 mbar. 10.0 g of 5,5-dimethyl-4,5-dihydroisoxazole were obtained, 89% pure according to $^1$H NMR (66%).

$^1$H NMR (CDCl$_3$): 1.40 (s, 6H), 2.75 (d, 2H), 7.06 (br s, 1H).

Example 2

Acid-Base Catalysis

Synthesis of 5,5-dimethyl-4,5-dihydroisoxazole 50.0 g (0.684 mol; 100 mol %) of acetone oxime were admixed with 62.6 g (0.744 mol, 109 mol %) of 3-methyl-2-butenal and cooled to 10-15° C. Over the course of 48 h, 1.5 g (6.8 mmol, 1 mol %) of N-methylanilinium trifluoroacetate were added to this mixture in 0.1 g portions. The product of value was subsequently isolated from the reaction mixture by fractional distillation under reduced pressure. Boiling point 44-48° C. at 17-18 mbar. 56.9 g of 5,5-dimethyl-4,5-dihydroisoxazole were obtained, >91% pure according to $^1$H NMR (76%).

$^1$H NMR (CDCl$_3$): 1.40 (s, 6H), 2.75 (d, 2H), 7.06 (br s, 1H).

Example 3

Acid Catalysis

Synthesis of 5,5-dimethyl-4,5-dihydroisoxazole 4.35 g of acetone oxime (59.5 mmol, 100 mol %) and 5.27 g of 3-methyl-2-butenal (62.6 mmol, 105 mol %) were mixed, and 0.13 g of trifluoroacetic acid (1.1 mmol, 1.9 mol %) was added. The mixture was stirred at room temperature for 60 h and the product was distilled under reduced pressure (46° C., 18 mbar). 4.7 g of colorless oil were obtained, with a purity of >95% according to NMR (45.0 mmol, 76%).

Example 4

Acid-Base Catalysis

Synthesis of 5,5-dimethyl-4,5-dihydroisoxazole 0.4 g of (2S,5S)-2-tert-butyl-3-methyl-5-benzyl-4-imidazolinone (1.6 mmol, 1 mol %) was initially charged in 50 ml of n-pentane, and 0.19 g of trifluoroacetic acid (1.6 mmol, 1 mol %) was added at 0° C. The mixture was stirred at −3-0° C. for 30 minutes. 11.9 g of acetone oxime (0.163 mol, 100 mol %) were added at 0° C. to the resulting suspension, the mixture was warmed to 20° C., and 16.5 g of 3-methyl-2-butenal (0.196 mol, 120 mol %) were added dropwise within 5 min. The mixture was stirred at this temperature for 16 h, and the product was isolated by distillation. 15.5 g of 5,5-dimethyl-4,5-dihydroisoxazole were obtained with a purity (GC) of 88%, corresponding to a yield of 84%.

Example 5

Synthesis of 3-chloro-4,5-dihydro-5,5-dimethylisoxazole 0.61 g (6.2 mmol, 100 mol %) of 4,5-dihydro-5,5-dimethylisoxazole were dissolved in 15 ml of carbon tetrachloride. Chlorine gas was introduced at 24-33° C. until the reactant had reacted fully. The solvent was driven off at 25° C. by a nitrogen stream. This gave 0.67 g of 3-chloro-4,5-dihydro-5,5-dimethylisoxazole as a colorless oil, according to GC and NMR with a purity of 90%, yield 75%.

$^1$H NMR (CDCl$_3$): 1.46 (s, 6H), 2.93 (s, 2H).

Example 6

Synthesis of [5,5-dimethyl(4,5-dihydroisoxazol-3-yl)]thiocarboxamidine Hydrochloride with Distilled Reactant 14.4 g (90% pure according to HPLC, 130 mmol, 100 mol %) of 4,5-dihydro-5,5-dimethylisoxazole were dissolved in 20 g of tert-butanol. Over the course of one hour, at 22-27° C., 12 g (170 mol, 130 mol %) of chlorine were injected from an immersed pipe and the solution was then purged with nitrogen for one hour. 7.1 g (93 mmol, 72 mol %) of thiourea were added in solid form and the reaction mixture was stirred at 20° C. for three hours. To complete the reaction, 1.0 g (13 mmol, 10 mol %) of thiourea were added and the mixture was stirred for 60 h hours. The solvent was removed under reduced pressure and the residue was suspended in petroleum ether. The residue was filtered off with suction and dried; final weight 26 g. A 10 g sample was recrystallized from isopropanol. This gave 6.2 g of the product as a colorless solid, yield 59%. Melting point 138-140° C.

Example 7

Synthesis of [5,5-dimethyl(4,5-dihydroisoxazol-3-yl)]thiocarboxamidine Hydrochloride Proceeding from 3-methyl-2-butenal 41.1 g (0.56 mol, 100 mol %) of acetone oxime were dissolved in 150 ml of chlorobenzene, and 1.0 g of N-methylanilinium triflate (4.5 mmol, 0.8 mol %) was added. Over the course of three hours, 48.7 g (0.58 mol, 103 mol %) of 3-methyl-2-butenal were added at a temperature of 20-23° C. The mixture was stirred at this temperature for 16 h and the acetone formed in the reaction was distilled off (50° C., 120 mbar). 93 g (1.31 mol, 230 mol %) of chlorine were injected at 0-5° C. over the course of 5 h. The solution was purged with nitrogen, 200 ml of ethanol were added and the temperature was increased to 45-50° C. 24.4 g (0.32 mol, 57 mol %) of thiourea were added a little at a time in solid form and the mixture was stirred at 20° C. for 16 h. Undissolved material was filtered off and ethanol was distilled off under reduced pressure until the crystallization of the product set in. A little acetone was added, and the product was filtered off and dried under reduced pressure. Yield 31.0 g (148 mmol, 26%) of fine white crystals, HPLC purity 99.3%.

$^1$H NMR (DMSO-d$_6$): 1.40 (s, 6H), 3.07 (s, 2H), 9.74 (br, 4H).

Example 8

Synthesis of [5,5-dimethyl(4,5-dihydroisoxazol-3-yl)]thiocarboxamidine Hydrochloride Proceeding from Acetone Oxime 0.37 g (3.5 mmol, 1.0 mol %) of N-methylaniline was dissolved in 60 g of n-pentane. At 0° C., 0.40 g (3.5 mmol, 1.0 mol %) of trifluoroacetic acid was added to this solution and the resulting suspension was stirred for 10 min. 25.0 g (0.342 mol, 100 mol %) of acetone oxime were added and the mixture was heated to 24-26° C. Subsequently, 29.4 g (0.350 mol, 102 mol %) of 3-methyl-2-butenal were added dropwise within 2 h, while the temperature was kept at 25° C. The mixture was stirred at 20° C. for 60 h and the reaction was completed by adding 1.5 g (18 mmol, 5 mol %) of 3-methyl-2-butenal in 16 h. The acetone formed was removed under reduced pressure, 80 g of tert-butanol were added and 10 g thereof were removed by distillation through a 20 cm Vigreux column. 26.0 g (0.366 mol, 107 mol %) of chlorine were injected through an immersed pipe at 15-20° C. within 2 h and the reaction mixture was subsequently purged with nitrogen for 15 min. 23.5 g (0.31 mol, 90 mol %) of thiourea were added a little at a time at 20° C. until HPLC showed complete conversion of the 3-chloro-4,5-dihydro-5,5-dimethylisoxazoline formed. The solvent was removed under reduced pressure, the residue was suspended in petroleum ether and the supernatant solution was discarded. The crude product was dissolved in 2.5:1 ethanol:chlorobenzene at 80° C., insoluble components were filtered off, the ethanol was removed under reduced pressure and the crystallization was initiated by cooling and adding acetone. The product was filtered, washed with acetone and dried under reduced pressure. This gave 39.2 g (0.187 mol, yield 55%) of [5,5-dimethyl(4,5-dihydroisoxazol-3-yl)]thiocarboxamidine hydrochloride as colorless crystals.

Melting point 146-147° C.

Example 9

Synthesis of 3-[(5-difluoromethoxy-1-methyl-3-trifluoromethylpyrazol-4-yl)-methylsulfonyl]-4,5-dihydro-5,5-dimethylisoxazole Proceeding from [5,5-dimethyl-(4,5-dihydroisoxazol-3-yl)]thiocarboxamidine Hydrochloride A) 3-[(5-Hydroxy-1-methyl-3-trifluoromethylpyrazol-4-yl)methylthio]-4,5-dihydro-5,5-dimethylisoxazole 1.49 g (97%, 36 mmol, 300 mol %) of sodium hydroxide were dissolved in 12 g of water and 2.0 g (12 mmol, 100 mol %) of 5-hydroxy-1-methyl-3-trifluoromethylpyrazole were added a little at a time. Formaldehyde solution (36.5% in water, 2.97 g, 36 mmol, 300 mol %) was added dropwise to the clear solution at 24° C. within 65 min and the mixture was stirred at this temperature for 90 min. Subsequently, 3.12 g (92% pure, 14 mmol, 120 mol %) of [5,5-dimethyl-(4,5-dihydroisoxazol-3-yl)]thiocarboxamidine hydrochloride, dissolved in 12.8 g of water, were added dropwise. The mixture was stirred at room temperature for 16 h. 5.9 g of hydrochloric acid (37%, 60 mmol, 500 mol %) were added at 14-18° C., followed by 12 ml of water. The mixture was stirred at room temperature for 16 h. The resulting precipitate was filtered off and washed twice with 10 ml each time of water and twice with 15 g each time of n-hexane. After drying, 3.08 g of a crystalline residue were obtained, which was used further without purification.

B) 3-[(5-Difluoromethoxy-1-methyl-3-trifluoromethylpyrazol-4-yl)methylthio]-4,5-dihydro-5,5-dimethylisoxazole The resulting residue (3.05 g, 10 mmol, 100 mol %) was dissolved in 30 ml of acetonitrile, 1.22 g (97%, 30 mmol, 250 mol %) of sodium hydroxide were added at 20-24° C. and the solution was stirred at 23° C. for 100 min. The mixture was cooled to 5° C. and 5.34 g (62 mmol, 620 mol %) of chlorodifluoromethane were injected at 5-15° C. within 45 min. The reaction mixture was stirred at room temperature for 60 h, and 15 ml of toluene and 15 ml of water were added. 1 ml of hydrochloric acid (37%) was added in order to bring insoluble constituents into solution. The organic phase was removed, the aqueous phase was extracted once again with 15 ml of toluene and the combined organic phases were washed with 15 ml of water and 15 ml of saturated sodium chloride solution. This gave 2.9 g of brownish oil, which was used further without purification.

C) 3-[(5-Difluoromethoxy-1-methyl-3-trifluoromethylpyrazol-4-yl)methylsulfonyl]-4,5-dihydro-5,5-dimethylisoxazole 2.8 g (7.8 mol) of the resulting oil were dissolved in 8 ml of acetic acid, and 80 mg (0.23 mmol, 3 mol %) of sodium tungstate dihydrate were added. Hydrogen peroxide (30%, 2.21 g, 20 mmol, 250 mol %) was added dropwise at 23-34° C. within 20 min and the mixture was stirred at room temperature for 16 h. The product was precipitated by adding 4 g of water and cooling to 1° C. After one hour at 10° C., the solids were filtered off and washed twice with 20 g each time of water and 20 ml of petroleum ether. This gave 1.0 g (2.6 mmol) of a solid.

$^1$H NMR (CDCl$_3$): 6.82 (t, 1H), 4.60 (s, 2H), 3.87 (s, 3H), 3.10 (s, 2H), 1.51 (s, 6H).

Comparative Example 1

Reaction of 5,5-dimethyl-4,5-dihydroisoxazole with Chlorine Gas in Ethanol 10.0 g (90.2%, 91.0 mmol, 100 mol %) of 5,5-dimethyl-4,5-dihydroisoxazole were dissolved in 20 g of ethanol. At 15-35° C., 12.0 g (169 mmol, 190 mol %) of chlorine were injected through an immersed pipe and the solution was subsequently purged with nitrogen for 1 h. According to qualitative HPLC/MS, a mixture of 3-ethoxy-5,5-dimethyl-4,5-dihydroisoxazole and 3-chloro-5,5-dimethyl-4,5-dihydroisoxazole in a ratio of 3.5:1 was obtained. The reaction mixture was admixed with 5.6 g (73.6 mmol, 81 mol %) of thiourea and the mixture was stirred at 22° C. for 16 h. The 3-ethoxy-5,5-dimethyl-4,5-dihydroisoxazole was not converted at this temperature and was present unchanged alongside large amounts of thiourea. The temperature was increased to 50° C. for 7 h, but even thereafter only traces of the desired [5,5-dimethyl(4,5-dihydroisoxazol-3-yl)]thiocarboxamidine hydrochloride, as well as decomposition products, were detected by HPLC.

Comparative Example 2

Influence of Acid in Step ii), the Reaction with Thiourea 0.5 g (91.4% pure, 3.4 mmol) of freshly distilled 3-chloro-4,5-dihydro-5,5-dimethylisoxazole was dissolved in 5 g of tert-butanol and admixed at 25° C. with 0.25 g (3.3 mmol) of thiourea and 3 drops of 32% hydrochloric acid. Reaction monitoring by HPLC showed, after 3.5 h, a conversion to [5,5-dimethyl(4,5-dihydroisoxazol-3-yl)]thiocarboxamidine hydrochloride of 39%. In an identically treated comparative sample without addition of hydrochloric acid, no conversion to the product was found after 3.5 h.

The invention claimed is:

1. A process for preparing 5,5-disubstituted 4,5-dihydroisoxazole-3-thiocarboxamidine salts of the formula (I) where

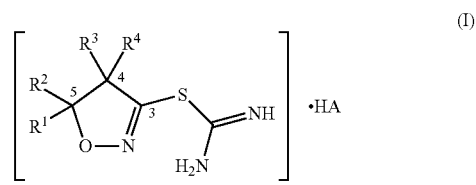

$R^1$ and $R^2$ are each independently $C_1$-$C_6$-alkyl or $C_1$-$C_4$-haloalkyl; or $R^1$ and $R^2$ together form a $C_2$-$C_5$-alkanediyl chain which may be mono- to tetrasubstituted by $C_1$-$C_4$-alkyl and/or may be interrupted by oxygen or by optionally $C_1$-$C_4$-alkyl-substituted nitrogen;

$R^3$ and $R^4$ are each hydrogen; and

A is chlorine or bromine;

comprising i) reacting a compound of formula (II) with a chlorinating or brominating reagent to give a compound of formula (III)

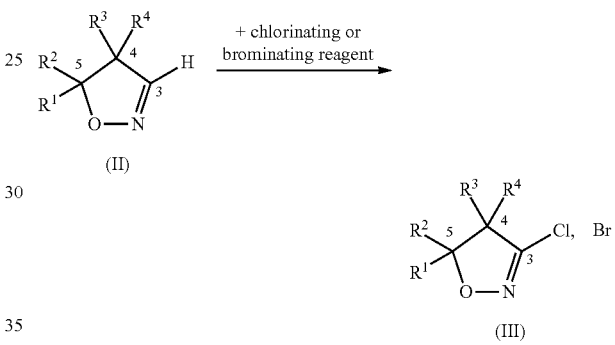

ii) reacting the compound of formula (III) with thiourea to give the compounds of the formula (I);

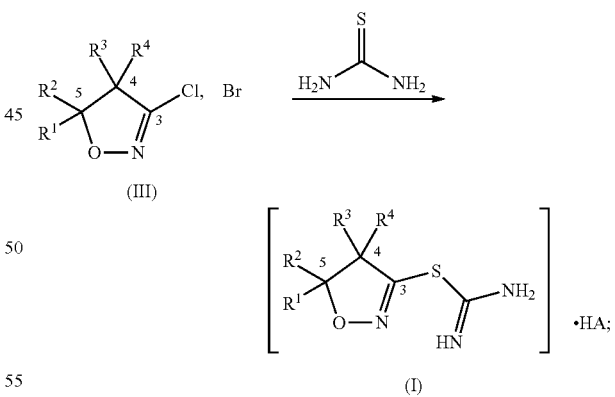

wherein the compound of formula (II) is prepared in a preliminary stage by reaction of a compound of formula (AII)

wherein
R$^a$ and R$^b$ are each independently hydrogen, C$_1$-C$_6$-alkyl, C$_1$-C$_4$-alkylcarbonyl, hydroxyimino-C$_1$-C$_4$-alkyl, phenyl, phenyl-C$_1$-C$_4$-alkyl or phenyl-C$_2$-C$_4$-alkenyl, where the phenyl rings may be mono- or polysubstituted by C$_1$-C$_4$-alkyl, C$_1$-C$_4$-alkoxy, di-C$_1$-C$_4$-alkylamino, halogen, hydroxyl or nitro; or R$^a$ and R$^b$ together form a C$_2$-C$_5$-alkanediyl chain;
with a compound of formula (AIII)

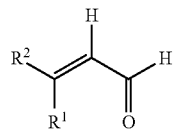

(AIII)

in the presence of an acid catalyst or of an acid-base catalyst and optionally in the presence of an organic solvent.

2. The process according to claim 1, wherein the chlorinating or brominating reagent used is elemental chlorine or bromine.

3. The process according to claim 1, wherein
R$^1$ is C$_1$-C$_4$-alkyl;
R$^2$ is C$_1$-C$_4$-alkyl;
R$^3$ is hydrogen; and
R$^4$ is hydrogen.

4. The process according to claim 3, wherein the chlorinating or brominating reagent used is elemental chlorine or bromine.

5. The process according to claim 1, wherein
R$^1$ is methyl;
R$^2$ is methyl;
R$^3$ is hydrogen; and
R$^4$ is hydrogen.

6. The process according to claim 5, wherein the chlorinating or brominating reagent used is elemental chlorine or bromine.

7. The process according to claim 5, wherein steps i) and ii) are performed in the same solvent.

8. The process according to claim 7, wherein the solvent for steps i) and ii) is tert-butanol.

9. The process according to claim 8, wherein the chlorinating or brominating reagent used is elemental chlorine or bromine.

10. The process according to claim 1, wherein the reaction product from step i), the compound of formula (III), is reacted directly without purification in step ii) with thiourea to give the compound of formula (I).

11. The process according to claim 10, wherein steps i) and ii) are performed in a one-pot process.

* * * * *